United States Patent [19]

Liu

[11] Patent Number: 4,551,552

[45] Date of Patent: Nov. 5, 1985

[54] PROCESS FOR PREPARING RIMANTADINE

[75] Inventor: John J. Liu, Newark, Del.

[73] Assignee: E. I. Du Pont de Nemours and Company, Wilmington, Del.

[21] Appl. No.: 613,374

[22] Filed: May 23, 1984

[51] Int. Cl.$^4$ ............................................. C07C 85/11
[52] U.S. Cl. ...................................... 564/448; 564/453; 564/456
[58] Field of Search ........................ 564/448, 453, 456

[56] References Cited

U.S. PATENT DOCUMENTS

| | | | |
|---|---|---|---|
| 3,352,912 | 11/1967 | Prichard | 564/453 |
| 4,100,170 | 6/1978 | Shetty | 424/325 |
| 4,248,891 | 2/1981 | Inamoto et al. | 564/455 |

OTHER PUBLICATIONS

Synthetic Methods of Organic Chemistry, W. Theilheimer vol. 9, p. 17, (1955).
Synthetic Methods of Org. Chem., W. Theilheimer, vol. 18, p.15, (1964).
P. E. Aldrich et al., Antiviral Agents. Structure-Activity Relationships of Compounds Related to 1-Adamontanamine, J. Med. Chem., 14(6), 535-43, (1971).

Primary Examiner—Charles F. Warren
Assistant Examiner—John A. Sopp

[57] ABSTRACT

A low temperature and pressure process for preparing rimantadine in high yields from 1-adamantyl methyl ketoxime is provided. The process comprises contacting a solution of the ketoxime with hydrogen in the presence of a platinum on carbon catalyst at a low temperature and pressure, e.g., room temperature and a pressure of about 25-115 psia (170-790 KPa) are preferred.

6 Claims, No Drawings

PROCESS FOR PREPARING RIMANTADINE

BACKGROUND OF THE INVENTION

1. Field of Invention:

This invention relates to processes for preparing rimantadine and more particularly to low temperature and pressure processes from 1-adamantyl methyl ketoxime.

2. Prior Art:

Pharmaceutical compositions containing α-methyl-1-adamantanemethylamine or the hydrochloride salt thereof (both herein referred to as rimantadine) are useful antiviral agents in animals. Rimantadine and related compounds useful as antivirals were first described by Prichard in U.S. Pat. Nos. 3,352,912 and 3,592,934. Both patents describe the preparation of rimantadine from the corresponding ketone oxime by reduction with lithium aluminum hydride. This preparation is also described in Aldrich et al., J. Med. Chem., 14, 535 (1971). Although this procedure is satisfactory in the laboratory, the high cost of this reducing agent and the danger of handling it on a large scale make this process unappealing as a commercial process.

Brake in U.S. Pat. No. 3,489,802 describes the preparation of rimantadine by the reductive amination of the corresponding acetyl compound. In this process, the acetyl compound, hydrogen, ammonia and catalyst (cobalt, ruthenium, or nickel) are reacted at temperatures up to 250° C., e.g., 140°-250° C., and pressures up to 15,000 psi, e.g., 500-2000 psi. This process on a commercial scale would require expensive, special reductive amination equipment.

Another rimantadine preparation process is described by Polis and Grava in U.S. Pat. No. 3,852,352. This is a Leuckart-Wallach reaction in which rimantadine is prepared by reacting 1-adamantyl methyl ketone with ammonium formate, formamide, or a mixture of formamide or acetamide with formic acid. Generally, yeilds are low (up to 82% by weight) and workup is tedious.

Shetty in U.S. Pat. No. 4,100,170 describes the reduction of 1-adamantyl-2-propanone oxime with hydrogen at 40 psig over $PtO_2$ in acetic acid. $PtO_2$ as a catalyst, however, has several disadvantages such as lower yield, higher cost and slower reaction which make it unsatisfactory for use in the preparation of rimantadine.

There is a need in the art for a high yield, low cost and safe process for the manufacture of rimantadine.

SUMMARY OF THE INVENTION

According to the present invention there is provided in a process for the preparation of rimantadine by the reduction of 1-adamantyl methyl ketoxime, the improvement comprising reducing the ketoxime by contacting a solution of the ketoxime with hydrogen in the presence of a platinum on carbon catalyst at a temperature in the range of about 10°-60° C. and a pressure of about 25 to 215 psia (170-1500 KPa).

As used herein psia=pounds per square inch absolute pressure and KPa=pressure in kilopascals.

DETAILED DESCRIPTION OF THE INVENTION

The process of the present invention provides a low temperature and pressure process for preparing rimantadine in high yields from 1-adamantyl methyl ketoxime according to the following reaction scheme:

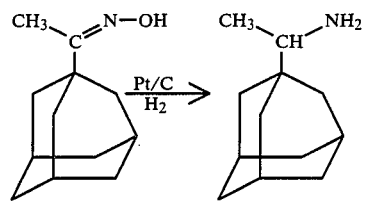

The starting ketoxime can be prepared according to any procedure known in the art. For example, it can be prepared by reacting 1-adamantyl methyl ketone with hydroxylamine hydrochloride as shown in Example 11 of U.S. Pat. No. 3,352,912. The ketone is available commercially or can be prepared as shown in the art.

The platinum on carbon catalyst used in the present hydrogenation process can be any of the many well-known such catalysts. While the particular composition of the catalyst is not believed to be critical, a particularly useful catalyst has been found to be 5% by weight platinum metal on carbon black particles sold by Johnson Matthey Inc. under the name Type 18MA. In general, such catalysts may contain about 2 to 20% by weight platinum on carbon based on the total weight of catalyst.

The hydrogenation reaction is conducted at a temperature in the range of about 10° to 60° C., preferably about 10° to 30° C., and a pressure in the range of about 25 to 215 psia (170-1500 KPa). It has been found that the reaction is conveniently carried out at room temperature and a pressure of about 25 to 115 psia (170-790 KPa). As with most reactions, reaction time can be decreased with an increase in temperature and pressure. However, this should not be done to the extent that the reaction may get out of control or the yield of product is reduced. In large scale reactions, it has been found most convenient to use an initial pressure of about 25 psia (170 KPa) and increase the hydrogen pressure to about 115 psia (790 KPa) after the initial exotherm has subsided. By conducting the reaction according to the preferred conditions, yields in excess of 95% based on the starting ketoxime have been obtained.

Suitable solvents for the hydrogenation are protic solvents such as alcohols, preferably ethanol, methanol, propanol and isopropanol. It is preferred that the solution be on the acidic side, i.e., pH of 1 to 5. Thus, a small amount of any acid which does not interfere with the reaction can be added to the reaction mixture. Mineral acids such as HCl, are preferred because of their low cost; however, organic acids such as acetic acid can also be employed. Alternatively, an organic acid, such as acetic acid or propionic acid may be used as solvent. Glacial acetic acid is the preferred solvent.

The invention can be further understood by reference to the following examples in which parts and percentages are by weight.

EXAMPLE 1

Into a Parr hydrogenation flask were placed 0.35 g of 5% Pt/C, 1.9 g of 1-adamantyl methyl ketoxime, 230 ml of ethanol and 2.0 ml of conc. hydrochloric acid. The flask was purged with hydrogen and then the hydrogenation reaction was initiated. Pressure was set at 34 psia (234 KPa) at ambient temperature and the reaction conducted overnight. The catalyst was removed by filtration and washed with 50 ml ethanol. The combined ethanol solution was distilled to dryness under vacuum. The remaining white solid was dissolved in 70 ml of water, and extracted twice with 50 ml ether. The ether layer was discarded. The aqueous layer was basified to pH 10-13 with sodium hydroxide and extracted twice with 100 ml of ether. The ether layer was dried over potassium hydroxide and magnesium sulfate which was removed by filtration. The dried ether layer was treated with hydrogen chloride gas and rimantadine hydrochloride precipitated. The solid was collected by filtration and dried to give 1.6 g of rimantadine hydrochloride (75% yield).

EXAMPLE 2

Into a Parr hydrogenation flask were placed 8.0 g of 1-adamantyl methyl ketoxime, 200 ml of glacial acetic acid, and 2.8 g of 5% Pt/C. Hydrogenation was continued overnight at 39 psia (270 KPa) and at ambient temperature. The catalyst was removed by filtration and the acetic acid solution was concentrated to one-third of the original volume by vacuum distillation. Water, 200 ml, was added to this conc. acetic acid solution and it was made basic with sodium hydroxide to give a milky solution. The milky solution was extracted three times with 100 ml of methylene chloride. The combined methylene chloride layer was dried over magnesium sulfate which was removed by filtration. The methylene chloride solution was distilled under vacuum to give 7.1 g of clear liquid rimantadine free base (96% yield).

EXAMPLE 3

Into a Parr hydrogenation flask were placed 13.7 g 1-adamantyl methyl ketoxime, 4.0 g 5% Pt/C, and 200 ml glacial acetic acid. The flask was purged with hydrogen and the hydrogenation continued for 2.25 hours under 30-35 psia (200-240 KPa) hydrogen pressure at room temperature. The hydrogen intake stopped after this duration but the flask was left overnight. The catalyst was removed and the acetic acid solution concentrated to approximately one-third the original volume by vacuum distillation. Water, 150 ml, was added and the mixture was basified with sodium hydroxide to give a milky solution. The milky solution was extracted twice with 100 ml methylene chloride. The methylene chloride solution was dried over magnesium sulfate, which was removed by filtration. The clear methylene chloride solution was treated with hydrogen chloride gas and a white solid formed. This mixture was treated with 100 ml ethyl acetate and more solid was formed. The solid was collected by filtration; a total of 11.4 g of rimantadine hydrochloride was obtained (75% yield).

EXAMPLE 4

A mixture consisting of 4.0 g of 5% Pt/C, 16.0 g of 1-adamantyl methyl ketoxime and 100 ml of glacial acetic acid was placed in a Parr hydrogenation flask. The system was purged with hydrogen under 35 psia (240 KPa) at room temperature. The hydrogenation was continued overnight. The catalyst was filtered and the filtrate was concentrated to one-third of its original volume at 72° C. under vacuum (10-20 mm). To this concentrated acetic acid solution, 400 ml ethyl acetate was added. Hydrogen chloride gas was bubbled into the ethyl acetate solution and a white solid precipitated. The white solid was collected by filtration to give 17.1 g of rimantadine hydrochloride (96% yield).

CONTROL EXAMPLE

1-Adamantyl methyl ketoxime, 2.0 g, was dissolved in 200 ml of ethanol and mixed with 1.0 ml of conc. hydrochloric acid. This solution was poured into a Parr hydrogenation flask, and 1.0 g of $PtO_2$ was added. Hydrogenation under 35 psia (240 KPa) and at room temperature proceeded slowly. After two days of hydrogenation, the catalyst was removed. The filtrate was distilled to dryness and 100 ml water was added to the residue. The insoluble material was removed by filtration and the aqueous layer was basified with sodium hydroxide. The aqueous layer was extracted with ether and the ether layer was separated. The ether layer was then dried over potassium hydroxide pellets and then magnesium sulfate. The resultant ether solution was distilled to remove the solvent providing 1.0 g rimantadine free base (54% yield).

$PtO_2$ is not desirable for commercial use as can be seen from this Control Example due to slow hydrogenation and low yield. In addition, $PtO_2$ is more expensive than a platinum on carbon catalyst.

What is claimed is:

1. In a process for the preparation of rimantadine by the reduction of 1-adamantyl methyl ketoxime, the improvement comprising reducing the ketoxime by contacting a solution of the ketoxime with hydrogen in the presence of a platinum on carbon catalyst at a temperature in the range of about 10°-60° C. and a pressure of about 25 to 215 psia (170-1500 KPa).

2. The process of claim 1 wherein the temperature is in the range of about 10°-30° C. and the pressure is in the range of about 25 psia (170 KPa) to about 115 psia (790 KPa).

3. The process of claim 2 wherein the ketoxime solution is selected from the group of ketoxime dissolved in an acid and ketoxime dissolved in an acidified protic solvent.

4. The process of claim 3 wherein the acid is glacial acetic acid and the protic solvent is ethyl alcohol.

5. The process of claim 3 wherein the catalyst is about 4 to 6 percent by weight platinum deposited on particles of carbon black.

6. In a process for the preparation of rimantadine by the reduction of 1-adamantyl methyl ketoxime, the improvement comprising contacting in a pressurized reaction zone a solution of the ketoxime in acetic acid with hydrogen in the presence of a platinum on carbon catalyst at a temperature in the range of about 10°-30° C. and a pressure in the range of about 25-115 psia (170-790 KPa), and recovering rimantadine from the resulting reaction mixture.

* * * * *